United States Patent [19]

Tober et al.

[11] Patent Number: 5,681,292

[45] Date of Patent: Oct. 28, 1997

[54] RETRACTABLE NEEDLE AND SYRINGE COMBINATION

[75] Inventors: John E. Tober, Miami Beach; Dennis J. Gordon, Cooper City; Douglas Couvertier, Fort Lovderdale, all of Fla.

[73] Assignee: Retrax Safety Systems, Inc., Miami, Fla.

[21] Appl. No.: 739,282

[22] Filed: Oct. 29, 1996

[51] Int. Cl.⁶ .................................................. A61M 5/32
[52] U.S. Cl. ................................. 604/195; 604/110
[58] Field of Search ........................ 604/195, 110, 604/218, 263, 240, 241, 134–138, 222

[56] References Cited

U.S. PATENT DOCUMENTS

| | | | |
|---|---|---|---|
| 5,092,853 | 3/1992 | Couvertier, II | 604/195 |
| 5,180,369 | 1/1993 | Dysarz | 604/110 |
| 5,211,628 | 5/1993 | Marshall | 604/110 |
| 5,324,265 | 6/1994 | Murray et al. | |
| 5,330,430 | 7/1994 | Sullivan | 604/134 |
| 5,385,551 | 1/1995 | Shaw | |
| 5,389,076 | 2/1995 | Shaw | |
| 5,395,337 | 3/1995 | Clemens et al. | |
| 5,407,431 | 4/1995 | Botich et al. | |
| 5,407,436 | 4/1995 | Toft et al. | |

*Primary Examiner*—John D. Yasko
*Attorney, Agent, or Firm*—Longacre & White

[57] ABSTRACT

A combination syringe and needle are disclosed wherein the needle is mounted to a retractable element which retracts into the body of the syringe plunger. The needle is mounted to the retractor which is spring biased to retract the needle. The retraction is actuated by releasing the forward end of the retractor from engagement with a collet positioned on the forward end of the syringe inner barrel. The collet is configured so as to clamp the forward end of the retractor and only releases the forward end when the collet is pushed forwardly, expanded, and disengages the forward end of the needle retractor.

11 Claims, 5 Drawing Sheets

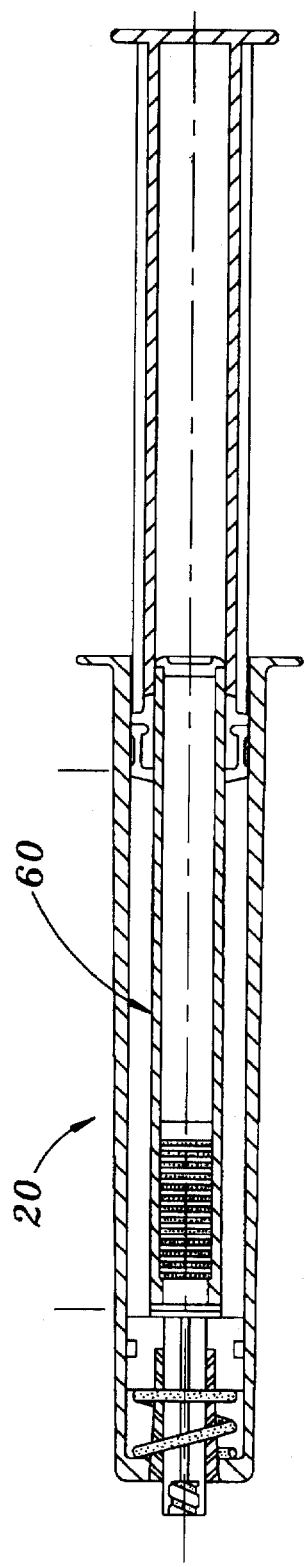
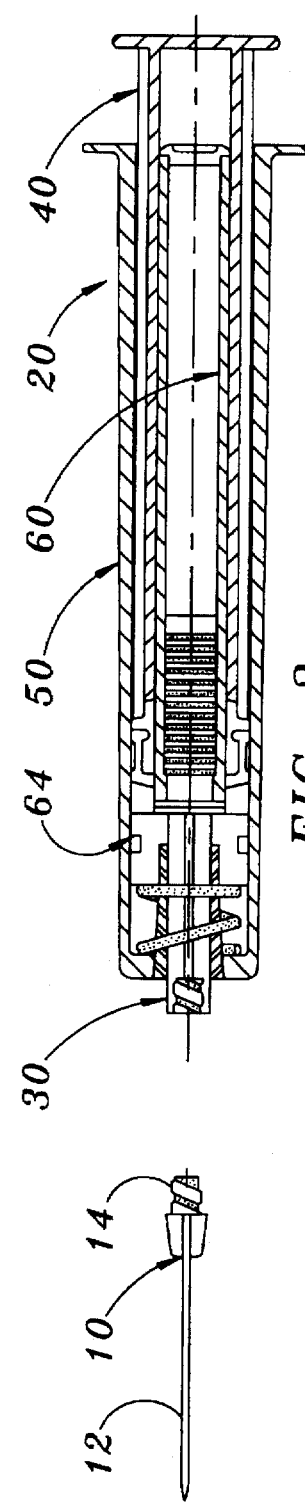
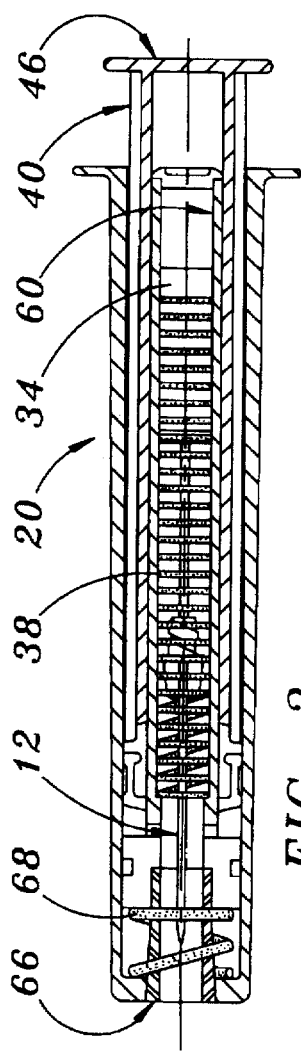
FIG. 1
FIG. 2
FIG. 3

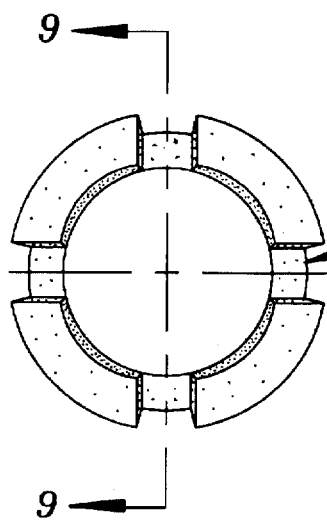
FIG. 8
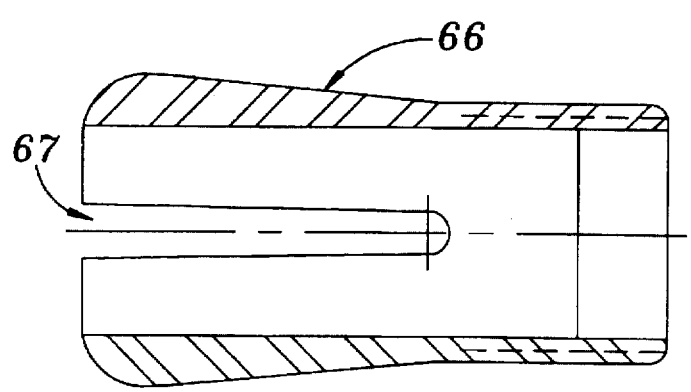
FIG. 9
FIG. 10
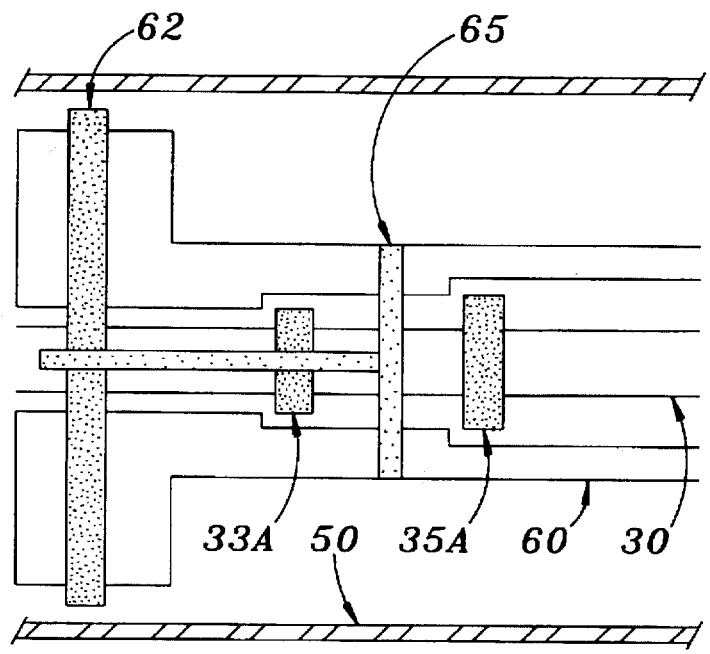

RETRACTABLE NEEDLE AND SYRINGE COMBINATION

FIELD OF THE INVENTION

The invention relates to medical devices including needles which are prevented, following use, from being in a position to stick a medical worker. More specifically, the invention relates to a combination device including a retractable needle and syringe which, following a full stroke of the syringe plunger, automatically retracts the needle into the body of the syringe thereby preventing the possibility of needle sticks.

BACKGROUND OF THE INVENTION

Since the identification of the needle stick as a significant risk to the health and well being of medical workers owing to the transfer of blood borne diseases, many devices have been proposed to eliminate or reduce this risk. While these devices have been theoretically manufacturable, from a practical standpoint many of the devices did not lend to mass production and/or economically feasible production. The problems associated with prior devices have included simply being too sophisticated to employing technology and techniques, for example molding tolerances, which could not be adapted to mass and/or economically feasible production.

Examples of prior art solutions to this problems abound in the art. U.S. Pat. No. 5,324,265 is one example of the prior art wherein the device relies on many separate seals and spring action to overcome the seal to retract the needle into a central portion of the plunger. The device also uses a special needle assembly and forward plug arrangement for the outer portion of the syringe. U.S. Pat. No. 5,385,551 discloses a syringe including a retractable needle which relies on a removable plug at the forward end of the plunger. The plug is displaced by the force of a spring carrying the needle into the body of the plunger. This device requires several specialized subassemblies to operate, including a specialized needle assembly.

U.S. Pat. No. 5,389,076 also discloses a combination syringe and retractable needle assembly. This device relies on the displacement of a forward ring seal along the length of the needle holder, whereby the needle holder is released rearwardly into the body of the plunger. This device also requires a specialized needle holder.

U.S. Pat. No. 5,395,337 discloses a combination syringe and needle similar in construction to the already mentioned U.S. Pat. No. 5,324,265 patent in that the device relies on spring action to break seal resistance and retract the needle into the body of the plunger. Many specialized components are necessary for use and assembly.

U.S. Pat. No. 5,407,431 also discloses a retractable needle and syringe type device (in this case a catheter insertion device). This device relies on a spreading collar surrounding a needle holder which, upon being spread by the forward movement of the plunger leading end, uses a spring loaded forward of the needle to push the needle into the plunger. Many specialized parts are required for assembly and use.

U.S. Pat. No. 5,407,436 discloses a retractable needle and syringe combination which relies on the forward push of the plunger to disengage the needle holder and send it, by spring action, rearwardly into the body of the syringe. The spring action must breach a seal in the central portion of the plunger and propel the needle rearwardly.

Many prior syringe and retractable needle combinations have also been proposed which use manual retrieval of the needle by the forward end of the plunger, whereupon the plunger is retracted and pulls the needle into the body of the syringe. These double action syringe and needle combinations have not been widely used. The reasons for this probably stem from the need for a two-handed or hand-toward-hand action being necessary on the part of the user to eliminate the risk of needle stick. The second manual step requires a person to grasp the outer body of the syringe and retract the needle against some resistance. This retraction could result in a slip on the part of the user and fouling of the needle against the user. Such techniques are generally prohibited by Federal safety regulations enacted by Congress to prevent needle stick injuries.

SUMMARY OF THE INVENTION

An object of the present invention is to simplify the structure necessary to create a one step one handed retractable needle and syringe combination. To the greatest extent possible the invention uses conventional apparatus. In addition, the user does not need to learn any procedure beyond what is necessary for conventional syringe and needle combinations.

The present retractable needle and syringe combination requires an extension of the stroke of the plunger to disengage the needle retractor from a forwardly located expanding collet. The collet expands and releases the spring biased needle retractor into the body of the syringe.

The needle for larger syringes is a conventional needle externally attached to a screw engaged assembly. The syringe includes a one piece inner barrel and forward sealing end with collet which is assembled with a single spring into the outer syringe barrel. A needle retractor and spring are then loaded into the syringe, followed by a plunger which completes the assembly. A total of two springs, three seals, and four plastic molded parts make up the specialized parts of the assembly. The balance of the commonly used components, ie, caps for needles, packaging for syringes, are all unmodified conventional off-the-shelf designs.

By virtue of the simplicity of componentry and use, the combination retractable needle and syringe of the present invention will be easily used, economically manufactured, and well adapted for mass use. Owing to these practical features, widespread use and disease prevention from the needle stick should be greatly reduced if not eliminated altogether.

BRIEF DESCRIPTION OF THE DRAWINGS

FIG. 1 is a partial sectional side view of a syringe according to the present invention;

FIG. 2 is a partial sectional side view of a syringe according to the present invention shown with the plunger in a forward position, a screw mounted needle according to the present invention is also shown;

FIG. 3 is a partial sectional side view of a combination syringe and needle according to the present invention shown in the retracted position;

FIG. 8 is an end view of the expanding collet used in the present invention;

FIG. 9 is a cross sectional view of the collet shown in FIG. 8 along section AA;

FIG. 10 shows an alternative seal arrangement of the needle retractor wherein the O-ring type seals have been replaced with static seals.

DETAILED DESCRIPTION

Figure 4:
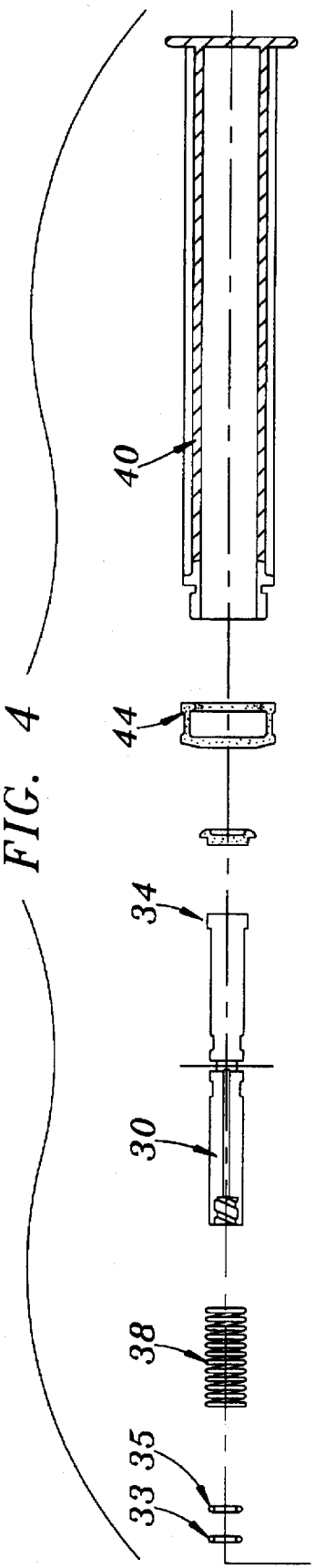
FIG. 4 is an exploded view of a syringe according to the present invention showing the assembly sequence of the component parts.
Figure 4:
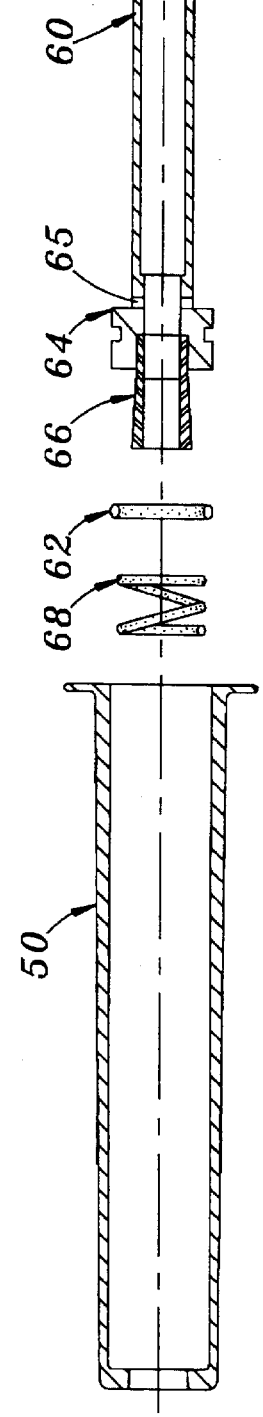
Figure 5:
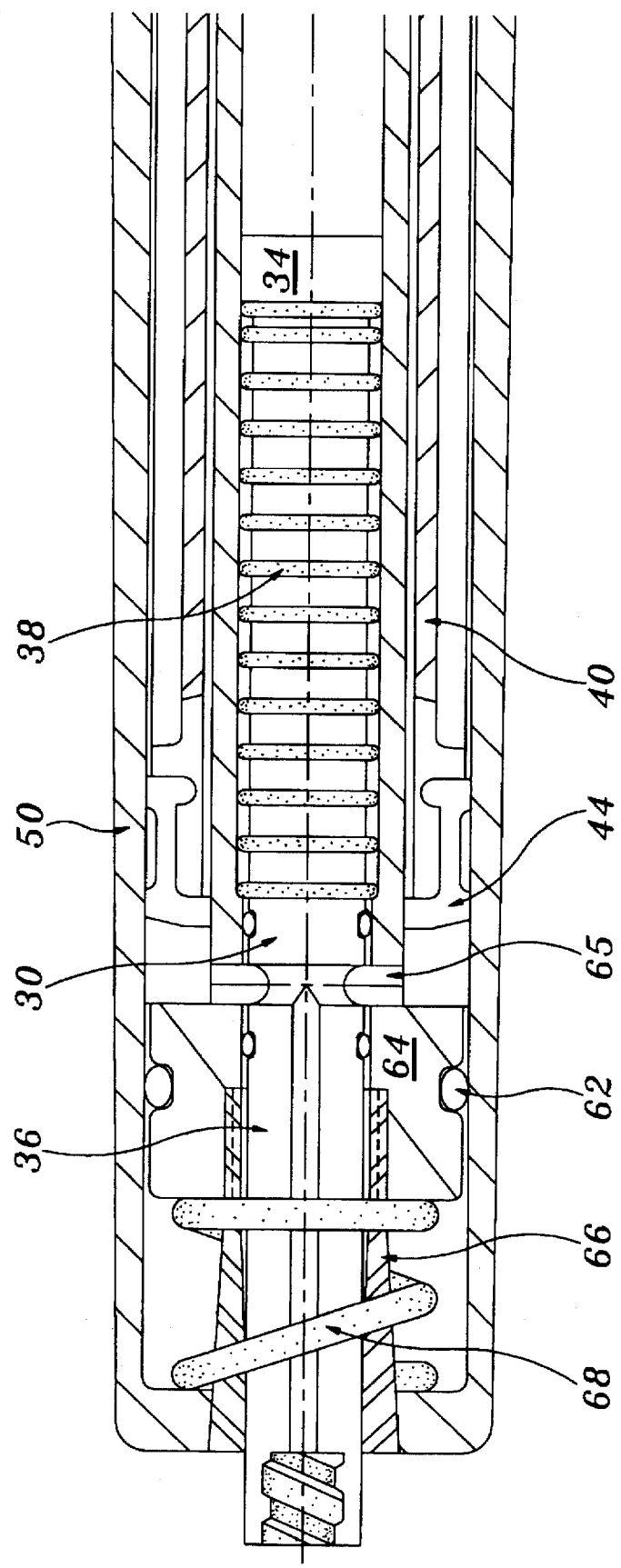
FIG. 5 is an enlarged partial sectional view of the forward end of an assembled syringe according to the present invention.

With reference to the drawing figures which form a part hereof, the following description is given. As shown in FIGS. 1–5, the invention is a combination syringe 20 and needle 10 device. In larger embodiments of the device, ie, syringes greater than 10 cc, the needle is a separately attachable member including a metal portion 12 and a screw attachment portion 14. For smaller syringes, for example home use devices, the needles are permanently attached to the syringe. These parts are adaptable to utilize a needle assembly which can be utilized on a conventional syringe with a male leur lcok component. The syringe 20 device of the invention includes a hollow inner barrel 60 which cooperates with a needle retractor 30 to withdraw the needle 10 into the inner barrel following use. The needle withdrawal action is accomplished by continuing the stroke of the syringe plunger 40, following the emptying of the syringe until the needle retractor 30 has been released from the collet 66 and propelled by spring action into the body of the inner barrel.

The syringe 20 is made up of an outer barrel or tube 50 and an inner barrel 60. The inner barrel has a forward end 64 which has an additional seal element 62, an O-ring in this embodiment, which seals the inner barrel to the inner surface of the outer barrel 50. This creates a fluid containment chamber which can be pressurized by the introduction of the plunger 40 into the containment chamber from the rearward end of the syringe. The plunger has a tubular body 40 and an annular plunger end 44 on a forward end of the plunger. At a rearward end of the plunger a push element 46 can be provided to engage a user's thumb.

The forward end 64 of the inner barrel 60 also includes a collet 66 which includes slots 67. The collet 66 has a slotted external funnel shape which creates a contracting and clamping effect for the collet as it is withdrawn through the opening located at the forward end of the outer tube 50. The collet is biased into a clamping or retracted position by a short spring 68 which biases the inner barrel 60 rearwardly with respect to outer tube 50.

Figure 6:
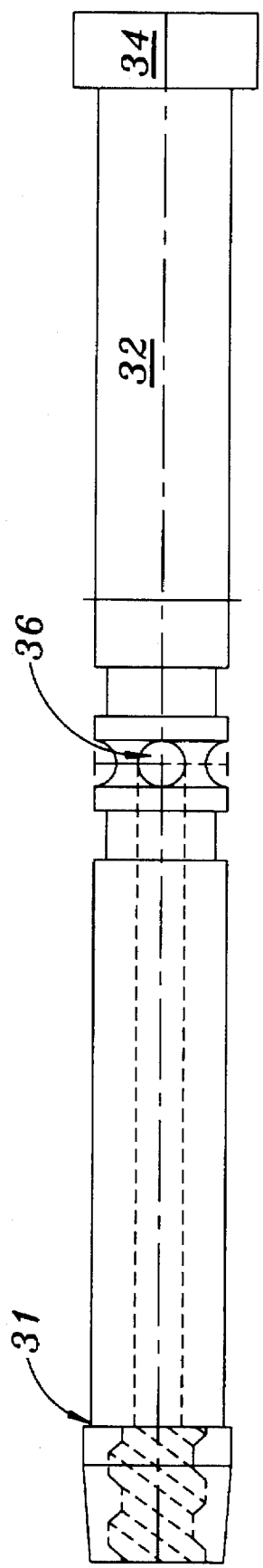
FIG. 6 is a plan view of the needle retractor of the present invention.
Figure 7:
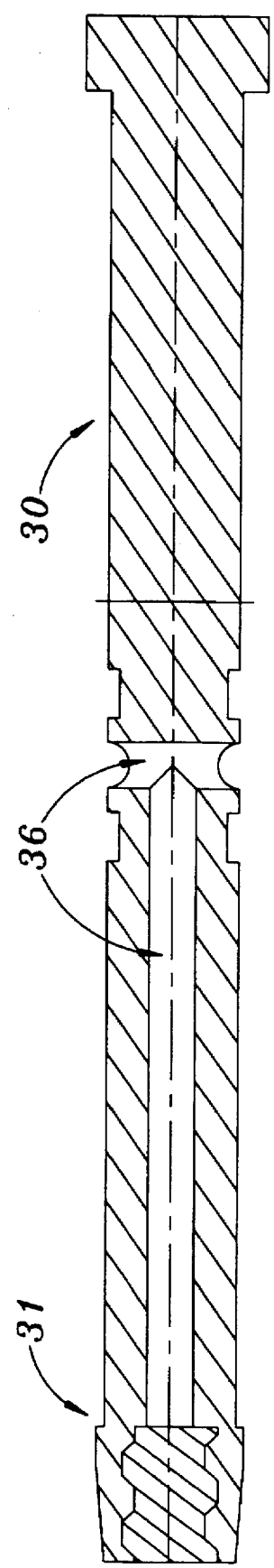
FIG. 7 is a sectional view of the needle retractor shown in FIG. 6.

The device further includes a retracting needle holder 30 shown in detail in FIGS. 6 and 7. The holder 30 is adapted to be inserted through the tubular body of the inner barrel 60 from a rearward end thereof. The holder 30 includes a body portion 32 with a end cap 34 on the rearward end thereof and a fluid port 36 located along a mid-section of the holder and extending to the forward end thereof. The retracting holder 30 passes fluid from the containment chamber upon pressurization thereof by the plunger 40 through the fluid port 65 of the inner barrel 60 through the holder fluid port 36 into the needle 10. The holder is sealed to the inner surfaces of the inner barrel 60 by two seals 33 and 35. In the first embodiment shown in FIGS. 1–7, the seals 33 and 35 are O-ring type seals. These are termed dynamic seals. An alternative embodiment of the sealing arrangement between the holder 30 and the inner barrel 60 is shown in FIG. 10 wherein static annular pressure seals are used between exterior annular edges of the holder 30 and interior annular diameter restrictions of the inner barrel 60.

Details of the collet 66 of this embodiment are shown in FIGS. 8 and 9. The collet includes slots 67 which allow for expansion and contraction of the collet as the exterior funnel shape of the collet is urged forwardly and rearwardly through the forward opening in the outer tube 50 of the syringe 20. When the collet 66 is urged rearwardly with respect to the outer tube 50 by short spring 68, the collet forward end shrinks in diameter and clamps onto the exterior of the holder 30. This clamping and retention of the holder is helped by the trap edge 31 which is present on the exterior of the holder 30. The collet 66 clamps onto the holder just behind the trap edge. The trap edge 31 is shown as an annular element in this embodiment, however it can take on any shape which binds against the restricting edges of collet 66 and retains the holder 30 in the forward end of the inner barrel 60.

The holder 30 is biased rearwardly by long spring 38 which pushes on the end cap 34 of the holder. To release the holder 30, the collet 66 is expanded by pushing the collet 66 forward by a push on the inner barrel forward end 64 by the forward end 44 of the plunger. When a user has dispensed the fluid by a full stroke on the plunger, the plunger is pushed past the full stroke position and the plunger end 44 urges against the inner barrel 64 which in turn pushes the collet 66 forward. By pushing forward, the collet 66 expands and the holder 30 disengages from the collet 66 and the holder 30 is propelled rearwardly into the tubular body of the inner barrel 60. The syringe 20 and needle 10 are then disabled with the needle trapped within the syringe as shown in FIG. 3.

The assembly sequence of the present invention is shown in FIG. 4. The plunger 40 and forward end 44 are assembled. The holder 30 and associated long spring 38 and seals 33, 35, are then inserted into the inner barrel 60 which is comprised of a forward end 64 and seal 62 and collet 66. The inner barrel and short spring 68 are loaded into the outer tube 50, followed by the insertion of the assembled holder 30. The holder is inserted until engagement with the collet occurs followed by the insertion of the assembled plunger. The entire syringe includes four polymer plastic molded parts, namely the plunger, outer and inner barrels, and the holder, three seals, and two springs. The seals can also be a polymer and consequently be molded together with the respective inner barrel and holder as desired. By virtue of the comparatively few numbers of parts and their simplicity in execution, the present syringe and retractable needle combination can be readily and economically manufactured.

The foregoing is a description of some of the preferred embodiments and best mode of the invention. Other versions of this invention can be created without departing from the spirit and scope of the invention which is limited only by the claims appended hereto.

We claim:

1. A syringe, comprising:

an outer barrel portion having a forward end and a rearward end;

an inner barrel adapted for insertion into the rearward end of said outer barrel, said inner barrel having an expandable collet mounted on a forward end thereof, and having a tubular body aligned with said collet, said collet having a forward end adapted to engage an opening in the forward end of said outer barrel, said opening constricting said collet as said collet is pulled rearwardly through said opening, said inner barrel being sealed to said outer barrel so as to contain fluid in a fluid containment chamber between an inner surface of said outer barrel and an exterior of said tubular body;

spring means positioned between said outer and inner barrels so as to bias said inner barrel rearwardly with respect to said outer barrel;

a needle retractor element having a forward end, adapted to receive a needle, and a shoulder trap edge, said forward end of said needle retractor having a diameter, said diameter of said needle retractor forward end being larger than a diameter of said needle, said needle retractor having a tubular body and a fluid port contained therein, inserted into said tubular body of said inner barrel and engaged by said expandable collet at said shoulder trap edge, said fluid port being in fluid communication with a fluid containment chamber defined between said outer barrel and said inner barrel;

second spring means for biasing said needle retractor rearwardly positioned between said inner barrel and said needle retractor; and, a plunger element adapted for insertion into said containment chamber for pressurizing any therein contained fluid and urging said fluid through said fluid port, whereby, at a user's discretion, forward movement of said inner barrel with respect to said outer barrel releases said needle retractor element rearwardly into said inner barrel.

2. A syringe as in claim 1, further comprising:

a needle connected to a forward end of said needle retractor element.

3. A syringe as in claim 2, further comprising:

screw attachment means for attaching said needle to a forward end of said needle retractor.

4. A syringe as in claim 1, wherein:

said spring means comprises a coil spring.

5. A syringe as in claim 1, wherein:

said second spring means comprises a coil spring.

6. A syringe as in claim 1, further comprising:

first separate seal means for sealing said outer barrel portion to said inner barrel.

7. A syringe as in claim 6, wherein:

said first separate seal means comprises an O-ring type seal.

8. A syringe as in claim 1, further comprising:

second and third separate seal means for sealing said needle retractor to said inner barrel.

9. A syringe as in claim 8, wherein:

said second and third separate seal means comprise O-ring type seals.

10. A syringe as in claim 8, wherein:

said second and third separate seal means comprise annular static seals.

11. A syringe as in claim 1, wherein:

said expandable collet has a funnel shaped exterior and includes slots in sides thereof to enable expansion and contraction of a longitudinal passageway located within said collet.

* * * * *

UNITED STATES PATENT AND TRADEMARK OFFICE
CERTIFICATE OF CORRECTION

PATENT NO. : 5,681,292

DATED : 10/28//97

INVENTOR(S) : TOBER, , John E.; GORDON, Dennis J; COUVERTIER, Douglas

It is certified that error appears in the above-identified patent and that said Letters Patent is hereby corrected as shown below:

At Column 3, Line 21, Please Change "lcok" to --lock--.

Signed and Sealed this

Eighteenth Day of August, 1998

Attest:

BRUCE LEHMAN

Attesting Officer

Commissioner of Patents and Trademarks